United States Patent
Sullivan et al.

(10) Patent No.: US 7,081,366 B2
(45) Date of Patent: Jul. 25, 2006

(54) UNIFORM BEAD DOSING FROM A STABLE DISPERSION

(75) Inventors: Brian M. Sullivan, Manhattan Beach, CA (US); Denes L. Zsolnay, Rolling Hills Estates, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 230 days.

(21) Appl. No.: 10/449,898

(22) Filed: Jun. 2, 2003

(65) Prior Publication Data
US 2004/0241884 A1    Dec. 2, 2004

(51) Int. Cl.
*G01N 33/553* (2006.01)

(52) U.S. Cl. .............. 436/526; 436/518; 436/173; 424/9; 424/1.29; 424/602; 128/653.4; 128/654; 514/492; 423/263; 423/301; 423/305; 252/359; 252/312; 44/51

(58) Field of Classification Search .............. 436/526, 436/518, 173; 424/9, 602, 1.29; 128/653.4, 128/654; 514/492; 423/263, 301, 305; 252/359, 252/312; 44/51; 149/46
See application file for complete search history.

(56) References Cited

U.S. PATENT DOCUMENTS

| | | | | |
|---|---|---|---|---|
| 3,985,649 A | * | 10/1976 | Eddelman | 210/695 |
| 4,430,251 A | * | 2/1984 | Patterson et al. | 366/349 |
| 5,344,640 A | * | 9/1994 | Deutsch et al. | 424/9.32 |
| 5,429,836 A | * | 7/1995 | Fuisz | 426/601 |
| 6,815,541 B1 | * | 11/2004 | Usui et al. | 536/25.41 |
| 2002/0137637 A1 | * | 9/2002 | Wojtecki | 508/161 |

* cited by examiner

*Primary Examiner*—James Housel
*Assistant Examiner*—Pensee T. Do
(74) *Attorney, Agent, or Firm*—Ronald M. Goldman; Connie M. Thousand

(57) ABSTRACT

A primary antibody bead suspension for an enzyme-linked immunoassay ("ELISA") procedure is formed of a quantity of primary antibody coated magnetic beads (3) uniformly dispersed and held in suspension (9) by a thixotropic non-Newtonian fluid (1). To remove the thixotropic non-Newtonian fluid prior to application in the ELISA procedure, a magnet (12) is placed against the side of the non-magnetic vessel (9) holding the suspension to draw the magnetic beads against the side while the thixotropic fluid is washed away by pumping (14,16,15 & 17) and replaced by a saline buffer solution.

2 Claims, 2 Drawing Sheets

UNIFORM BEAD DOSING FROM A STABLE DISPERSION

REFERENCE TO PRIOR APPLICATIONS

Reference is made to U.S. application Ser. No. 09/837,946, filed Apr. 19, 2001, entitled "Automated Computer Controlled Reporter Device for Conducting Immunoassay and Molecular Biology Procedures", copending herewith, the entire content of which is incorporated herein by reference. The benefit of 35 U.S.C. 120 is claimed with respect to the foregoing application of which the present application is a continuation-in-part.

FIELD OF THE INVENTION

This invention relates to a means of storage and handling of the primary antibody coated magnetic beads used in certain enzyme-linked immunoassay ("ELISA") procedures, and to enhance pump life in the pumps of an automated apparatus that performs the enzyme-linked immunoassay technique to conduct immunoassays and molecular biology procedures using antibody coated magnetic beads.

BACKGROUND

The ELISA procedure is a quantitative in vitro test for an antibody or antigen in which the test material is adsorbed on a surface and exposed to a complex of an enzyme linked to an antibody specific for the substance being tested for with a positive result indicated by a treatment yielding a color in proportion to the amount of antigen or antibody in the test material. The ELISA procedure is described more specifically, for one, in a book entitled Methods in Molecular Biology Vol 42, John R. Crowther, Humana Press, 1995. The antibody specific for the substance being tested for in the foregoing definition constitutes a recognition molecule. ELISA-like approaches using other recognition molecules can also be used, such as aptamers, DNA, RNA & molecular imprint polymers.

The basic definition of ELISA was expanded beyond the colometric approach, wherein color is used as an indicia, to include yielding a rate of change of voltage or current conductivity in proportion to the amount of antigen or antibody in the test material, a voltametric or amperiometric approach to detection. Patent Cooperation Treaty application PCT/US98/16714, filed Aug. 12, 1998 (International Publication No. WO99/07870), entitled "Electrochemical Reporter System for Detecting Analytical Immunoassay and Molecular Biology Procedures" (hereafter the "'16714 PCT application), claiming priority of U.S. patent applications Ser. Nos. 09/105,538 and 09/105,539"), describes both a colormetric and an electrochemical reporter system for detecting and quantifying enzymes and other bioagents in analytical and clinical applications.

The ELISA procedure has also been automated. In a prior application by the present applicants, Ser. No. 09/837,946, filed Apr. 19, 2001, entitled "Automated Computer Controlled Reporter Device for Conducting Immunoassay and Molecular Biology Procedures" (the "'946 application"), the content of which is incorporated herein by reference in its entirety, an automated analytic instrument, hereafter referred to sometimes as a biosensor instrument, is disclosed that tests whether a sample (e.g. the analyte) is or contains a respective bioagent, protein and/or nucleic acid using the ELISA technique.

The biosensor instrument described in the '946 application is computer-controlled and user-friendly, which permits relatively unskilled personnel to carry out important tests for the presence of a bioagent, protein and/or nucleic acid in a sample of suspect material. An electronic controller in the biosensor instrument, such as a programmed microcontroller, controls a series of pumps to automatically sequence pumping of the individual fluids required in the ELISA procedure into a cell (or cells) necessary to produce an electro-chemical reporter, analyzes the electro-chemical data and, ultimately, displays the concentration of the bioagent determined from that analysis. Once started, the apparatus, governed by the program of the microcontroller, conducts the test automatically without the necessity for human intervention. The biosensor instrument may be housed in a single package for easy portability; and may be either battery or line powered. The content of the prior application is referred to and incorporated herein in its entirety.

In preparation for a test of suspect material with the biosensor instrument, a solution is prepared by placing the suspect material in a water-based buffer, such as a phosphate buffered saline solution. The suspect material may have been preliminarily treated, such as by exposing the material to ultrasonic energy to break the material into multiple small clumps or even granules to ensure maximum surface area exposure of the sample in solution, or the suspect material may be used "as is" as collected.

In one of the initial steps of operation of the ELISA procedure carried out by the biosensor instrument, the sample solution, referred to as the analyte, is deposited into a container or vessel that contains a quantity of micron size magnetic beads in a saline solution (or vice-versa), referred to herein as a primary antibody solution (or "1° Ab"). The surface of those beads contains a coating of an antibody to the suspect bioagent, protein and/or nucleic acid. The particular antibodies used to coat the magnetic beads are known to bind to the bioagent, protein and/or nucleic acid of interest or of concern. That is, the antibody coating exhibits a chemical "stickiness" that is selective to specific bioagents, proteins and/or nucleic acids. The analyte and the magnetic beads are then mixed together in the liquid. Assuming that the analyte is the suspected bioagent, as example, the analyte should bind to the antibody coated on the beads, forming a 1° Ab/analyte complex.

To ensure that the analyte molecules are afforded the greatest opportunity to effectively bind with the molecules of antibody coating on a magnetic bead, it was found desirable to stir the magnetic bead solution, a slurry, before undertaking the foregoing step. Awaiting use, the coated magnetic beads are stored in the saline solution in a vessel and forms a weak slurry. Over time in storage, the force of gravity causes the beads to settle to the bottom of the storage vessel. For each analysis the contents of the bead reservoirs were, preferably, mixed to ensure that when the biosensor instrument withdrew a set volume from the storage vessel, the quantity of beads that is drawn into the reaction is also set. To stir (or mix) the coated magnetic beads the biosensor instrument pumped at least a portion of the contents from the vessel and alternately then pumped that portion back therein, doing so a number of times. That action ensured that the magnetic beads were adequately dispersed in the liquid.

Pumping of the magnetic beads increases wear and tear on the pumps and/or mixers. Further, if mixing is excessive, the beads could be damaged. That in turn limits the maximum number of doses that could be obtained before it was necessary to replenish (or replace) the beads. To maximize the time between required replenishment of the beads the duration of the each mixing cycle is minimized, trading off uniformity of bead dosage for endurance.

Electric pumps consume electrical energy during operation. They also tend to generate noise. Usually, the harder the pump must work, the greater is the noise produced and the electrical power consumed. Minimizing the number of pumps in the instrument, even reducing the number of pumps by one, enhances the ability of the instrument to operate on dry cell batteries or maximize the period over which rechargeable batteries can be used before requiring a recharge. Minimizing the number of pumps also reduces the noise generated by the instrument.

Accordingly, an object of the invention is to minimize or avoid the necessity of mixing or stirring of a saline solution of magnetic beads in order to achieve a relatively uniform dispersal of magnetic beads in a primary antibody bead system for an enzyme-linked immunoassay procedure.

Accordingly, a principal object of the present invention is to increase the uniformity of bead dosage without requiring increased mixing.

A further object of the invention is to reduce the amount of maintenance necessary to maintain pump operation in the biosensor instrument and enhance the operational life of that instrument.

And, a still further object of the invention is to minimize or eliminate the bead mixing operation in the biosensor instrument.

SUMMARY OF THE INVENTION

In accordance with the foregoing objects and advantages, a primary antibody bead suspension for use in an enzyme linked immunoassay ("ELISA") procedure contains a supply of primary antibody coated magnetic beads that are dispersed and suspended in a thixotropic non-Newtonian material, which serves as a suspension agent. The primary antibody bead suspension is stored in a container in which the suspension may be transported and/or stored for use when necessary in the ELISA procedure.

In accordance with a further aspect to the invention, at least a principal portion of the storage container is formed of non-magnetic material, such as glass or plastic. In accordance with a more specific aspect to the invention, the thixotropic non-Newtonian material comprises the common condiment known as catsup. In a still more specific aspect to the invention, the magnetic beads are of ferrite material and are spheres about four and one-half microns in diameter.

In accordance with a new method, in preparation for application in the ELISA procedure a magnet is placed against the side of the storage container to draw and hold the coated magnetic beads against a side wall, and, concurrently, a saline wash solution is alternately pumped into and sucked out of the storage container together with the thixotropic non-Newtonian suspension agent, cleansing the container of the suspension agent, while leaving the coated magnetic beads pressed alongside the container wall by the pull of the magnetic field. The magnet is removed and the magnetic beads are generally dispersed in the saline buffer solution.

The foregoing and additional objects and advantages of the invention, together with the structural characteristic thereof, which were only briefly summarized in the foregoing passages, will become more apparent to those skilled in the art upon reading the detailed description of a preferred embodiment of the invention, which follows in this specification, taken together with the illustrations thereof presented in the accompanying drawings.

DETAILED DESCRIPTION OF THE PREFERRED EMBODIMENTS

Figure 1:
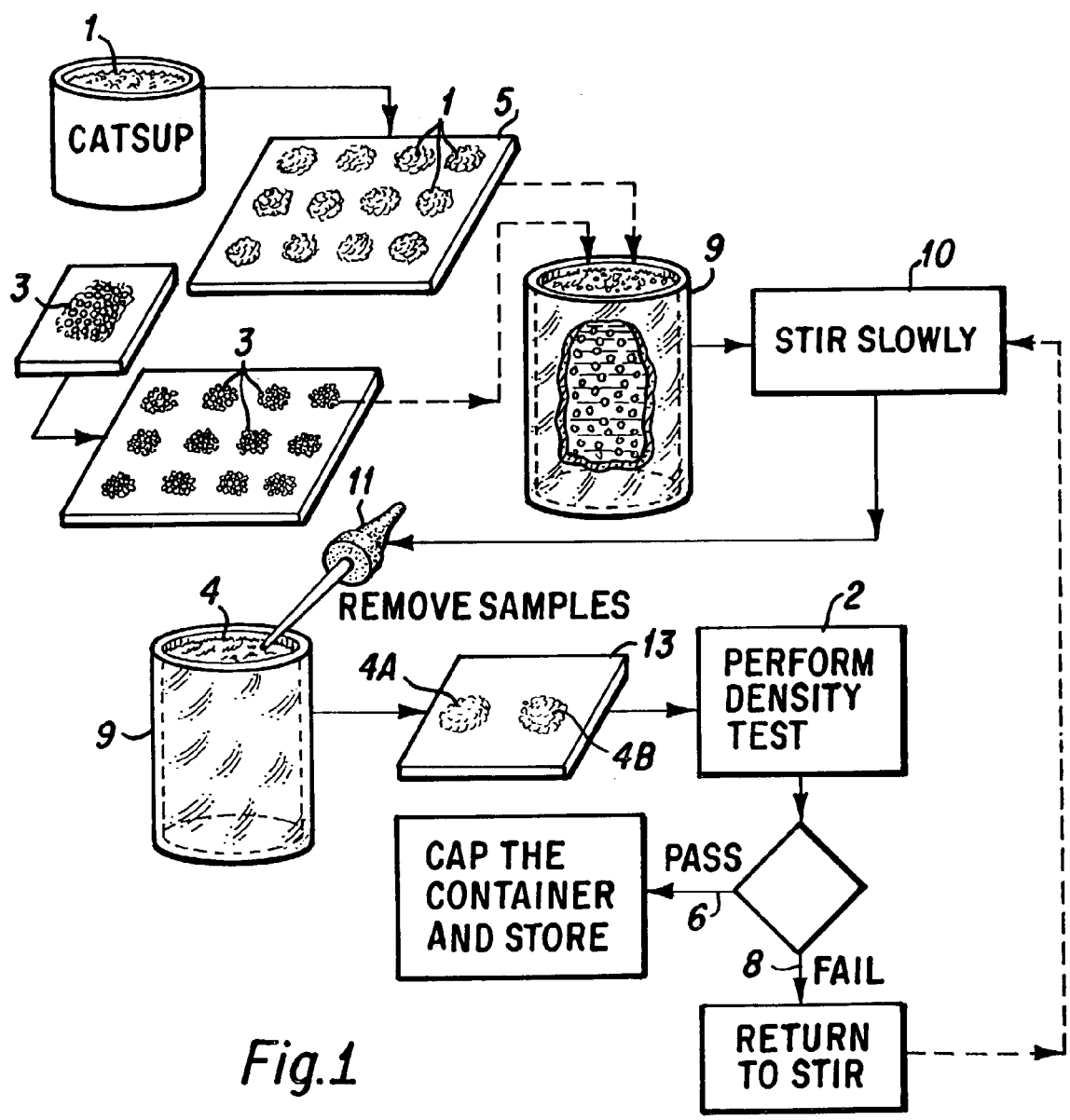
FIG. 1 illustrates the method of preparing and storing the primary antibody bead suspension.

Referring to FIG. 1, the process begins with a thixotropic non-Newtonian fluid, such as the familiar condiment catsup 1, and a supply of primary antibody coated magnetic beads 3. The two ingredients are set out, preferably in a sterile laboratory, and smaller quantities of each are then scooped from the main supply and placed on an appropriate plate. The quantity of magnetic beads is coated with the primary antibody using known techniques, such as that of Dynal Biotech Company, of Oslo Norway, a seller of beads for ELISA procedures, which supplies instructions for coating beads along with beads sold by the company.

The catsup, such as the familiar Heinz Ketchup brand catsup available in most grocery stores, being a foodstuff is not likely to be contaminated with bacteria or the like that could be harmful to the antibody coating or which would molecularly link to that antibody coating. Although the exact recipe for Heinz Ketchup is regarded as a trade secret by that company, the ingredients listed on a bottle of that widely available condiment include tomato concentrate from red ripe tomatoes, distilled vinegar, high fructose corn syrup, salt, spice, onion powder and natural flavorings. The catsup is removed from the container, which contains a supply of at least fifty micro-liters of Ketchup. About ten scoops of approximately five micro-liters each are separately deposited on plate 5 providing ten parts. A quantity of at least four million beads of a diameter of four and one-half microns of the primary antibody coated magnetic beads is also scooped from the supply in scoops of about four-tenths million beads and separately placed in ten separate portions on plate 7.

Each part of the catsup 1 is scooped from plate 5 and spooned into a one-milliliter cylindrical transparent glass or plastic flask 9. Each scoop of catsup is followed by one of the ten parts of the magnetic beads 3 from plate 7. Upon completion, the flask is filled, at least partially, with alternate layers of catsup and antibody coated magnetic beads. Then the content of the flask is carefully stirred 10 for a short while, about five minutes, suitably with a pipettor, not illustrated, to further disperse the magnetic beads within the catsup and form a more homogenous mixture 4 of catsup and beads with the beads remaining suspended in the catsup. Stiring is carried out slowly and carefully so as not to significantly reduce the viscosity of the catsup and cause the catsup to liquefy. That stirring is akin to the act of folding (instead of mixing) in preparing certain cakes.

The layering and stirring should more completely and uniformly distribute the beads within the catsup medium and provide a homogenous bead suspension. To be certain that the suspension is homogenous, a sample 4A is taken from the upper end of the mixture, suitably using an eyedropper 11 to suck up the portion, and deposit same on plate 13. A second portion 4B is taken from the bottom of the mixture. The two portions 4A and 4B are then separately analyzed, subjected to a density test 2 to determine the bead density in each part.

The bead density may be measured by washing the sample with a saline solution to remove the catsup from the sample, allowing the saline solution to evaporate or boiling the liquid off and then weighing the magnetic beads (and salt), which should be all that remains of the sample. Since the salt in both solutions should be the same, the difference in weight should be solely that of the magnetic beads. Other density testing methods may be used instead.

If the bead density of the two parts is approximately equal, then the mixture may be deemed homogenous and no further stirring is necessary, as represented by the "pass" designation 6 in the figure. If the density of the two parts is not approximately equal, represented by the "fail" designation 8, then resort is again made to the stirring step. Stirring is then continued for another five minutes, two more samples are taken, and the respective bead density in each of the two additional samples is determined, and the density comparison made. As before, if the density is approximately equal, then the preparation is complete; and, if not equal, the foregoing procedure is repeated again (and again) until one determines that the bead density in each of the pair of samples taken from the mixture is about equal. Once bead density in two samples is found to be at least approximately equal, represented by "pass", then the mixture may be deemed homogenous and the preparation is complete.

The end result is a primary antibody bead suspension containing primary antibody coated magnetic beads homogeneously dispersed and suspended in a thixotropic fluid. The open end of the cylindrical flask is then capped or sealed and the flask is stored for shipment and later use in an ELISA procedure, such as the automated ELISA procedure referred to in the '946 Application.

As is appreciated, an ELISA procedure may be used to detect many different bioagents, proteins and/or nucleic acids. To identify a particular one of those bioagents, proteins and/or nucleic acids requires an individual primary antibody known to link to that particular one. For increased versatility of application the laboratory or apparatus should have available for use a number of different primary antibody suspensions corresponding to the bioagents, proteins and/or nucleic acids anticipated to be of interest, and each of those may be prepared as a suspension in a thixotropic fluid in the manner described.

Figure 2:
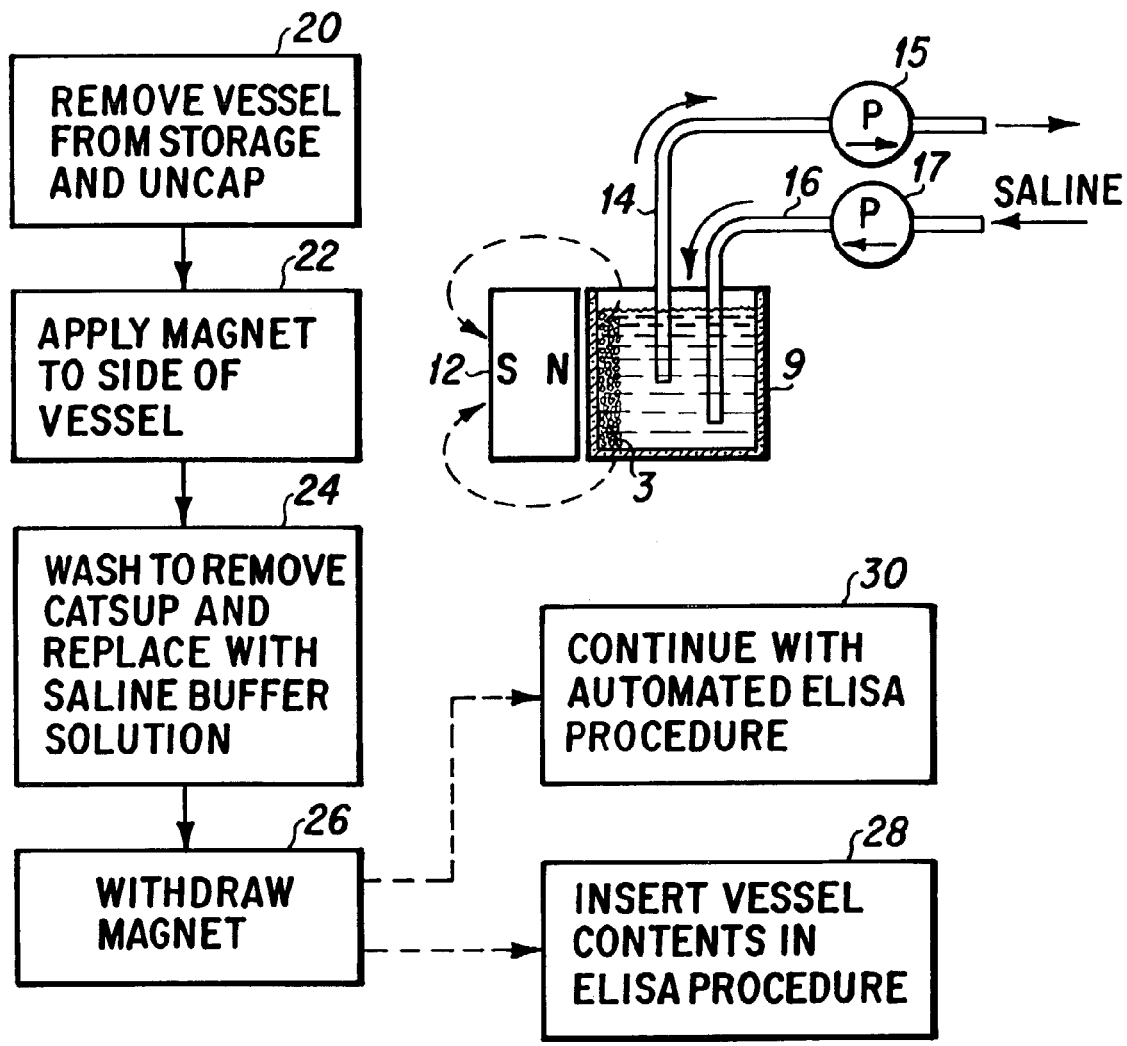
FIG. 2 illustrates the method of preparing the stored primary antibody bead suspension for application in the ELISA procedure.

Referring next to FIG. 2, when an ELISA procedure is to be performed to test a particular analyte to determine whether the analyte contains a particular bioagent or the like, the flask in which the antibody coated bead suspension for that particular bioagent or the like is stored is selected and opened 20. Initially, it was opined that the suspension could be used directly in the ELISA procedure since the catsup should not interfere chemically with any of the steps of the process. However, even though the initial step of the ELISA procedure would be to mix the analyte in with the suspension to have the analyte come in contact with and, if appropriate, link to the antibody coated on the magnetic beads. The mixing should essentially place the catsup under sufficient shear and render the catsup more liquid (e.g. less viscous), it was thought that the mixing would impose too great a burden on the automated test instrument and/or there would be insufficient contact between the analyte and the antibody coating on the beads. Because of those practical concerns such a procedure was deemed less preferred. Instead, the preferred approach was to prepare or condition the bead suspension, as illustrated in FIG. 2, to remove the catsup prior to use in the ELISA procedure and replace the catsup with a saline buffer solution.

A powerful permanent magnet (or electromagnet) 12 is placed alongside 22 the flask 9 to draw the coated magnetic beads 3 out of suspension in the catsup and force them against the wall of the flask adjacent the magnet. As illustrated the magnet has a pole that extends the length of the flask. The magnetic field draws the magnetic beads all along the flask wall so that the beads are not concentrated at any particular location. The transparent intake tube 14 of an electric suction pump 15 and the outlet tube 16 of an electric pump 17 are inserted within the catsup, distanced from the collected magnetic beads.

In the wash operation 24, pump 15 sucks out the catsup, while pump 17 pumps a saline buffer solution into the flask. In doing so the pump exerts a force on the thixotropic fluid that causes the viscosity of the fluid to decrease, that is, become more fluid. When the liquid being sucked through the intake tube 14 appears clear, that is, is sucking up the saline buffer that is being pumped in, then the catsup has been effectively removed and the magnetic beads washed. At that time, the pumps are turned off, pump 15 being turned off first, and pumping halts, leaving the flask filled with the saline buffer solution (and the primary antibody coated magnetic beads, which remain restrained by the magnetic field). Tubes 14 and 16 may be withdrawn from flask 9 and magnet 12 removed 26.

The removal of the magnet releases the coated magnetic beads into the saline solution in the flask. Due to the minute size of the magnetic beads and the turbulence and/or vibration of the saline solution, the magnetic beads remain relatively dispersed in the saline buffer solution. Since the beads in the solution are to be employed almost immediately in the ELISA procedure, the beads do not have sufficient time to agglomerate or gravitate to the bottom of the flask. The coated magnetic beads are ready to be intermingled with the analyte in the initial stage of the ELISA procedure. The foregoing operation requires the pumps to be operated for a shorter period than required for stirring up the bead slurry in the prior system, which saves wear and tear; and the pump and consumes less electricity. If the foregoing is to be treated as a stand-alone operation, the antibody coated magnetic beads (in the saline liquid) are applied to the analyte binding step of a manually performed ELISA procedure 28. Alternatively, when the foregoing is undertaken as initial steps in an automated ELISA procedure, such as that described in the '946 Application, the automated procedure continues 30 with the remaining steps, such as briefly reviewed hereafter.

The foregoing washing procedure provides empirical data on the time typically required to replace the thixotropic fluid with another Newtonian fluid, such as the saline buffer solution. That information may be used to reprogram the computer of the biosensor instrument described in the '946 Application that is incorporated herein. The biosensor instrument contains a magnet. In the course of operation of the biosensor instrument, the computer controlled controller positions the magnet against the side of a non-magnetic vessel to draw the magnetic beads against the side of the vessel to commence a wash operation of the formed 1° antibody/analyte complex. Liquid is then pumped from the container containing the foregoing complex and is replaced by liquid while the magnetic field of the magnet confines the magnetic beads against the side of the vessel. That pumping and replacement is continued for a sufficient period that was empirically determined (and programmed into the controller) to satisfactorily complete a wash. The same wash procedure can be performed to wash the thixotropic fluid from the suspension and replace that fluid with another through minor modifications in the program governing operation of the automated apparatus. That is, the program of the controller is modified to perform removal of the thixotropic fluid prior to depositing the analyte into the vessel. The remainder of the operation of the biosensor instrument remains as before.

As example, the non-magnetic vessel containing the antibody coated magnetic bead suspension is placed open in the automated apparatus and the pump intake and outlet tubes inserted. The vessel containing the analyte is placed in the proper location. On start of the controller operation, the controller moves the magnet into position against a side of the vessel with a magnetic pole confronting the side of the non-magnetic vessel. Then the thixotropic fluid is pumped out and clean saline solution is pumped in. That pumping is continued for the predetermined interval empirically determined by the designer to replace all or most of the thixotropic fluid with saline solution. The controller then halts pumping and moves the magnet away from the vessel, which releases the antibody coated magnetic beads to disperse into the solution. In the next step, formerly the initial step, the controller pumps the analyte into the foregoing vessel.

A non-Newtonian fluid is one whose flow behavior departs from that of an ideal newtonian fluid. McGraw Hill, Concise Encyclopedia of Science and Technology ($2^{nd}$ Ed.) broadly categorizes non-Newtonian fluids into three classes, specifically those fluids that are (1) time independent, wherein the rate of shear at any point in the fluid is some function of the shear stress at that point and depends on nothing else; (2) time dependent, wherein the relationship between shear stress and shear rates depends on the time the fluid was sheared, that is, on previous history; and (3) those that have the characteristic of both viscous liquids and elastic solids and exhibit partial elastic recovery after deformation, frequently called viscoelastic fluids.

According to that source, the time dependent fluids may be divided further into two classes, thixotropic fluids, in which the shear stress decreases with time when the fluid is sheared at a constant rate, and rheopectic fluids, in which the shear stress increases with time when the fluid is sheared at a constant rate. The catsup possesses the physical properties of the thixotropic fluid. Hence, the medium in which the coated magnetic beads are suspended is appropriately described as a thixotropic non-Newtonian fluid or, simply, thixotropic fluid.

It may be noted that Websters New Collegiate Dictionary, a general dictionary defines a thixotropic liquid simply as a fluid that has the property of various gels becoming fluid when disturbed (as by shaking). Though Webster's definition captures the gist of the effect of the fluid changing into a more liquid form when subjected to sufficient stress, an effect desired in the invention, because of the reference to a gel, that definition is seen to be less precise and unnecessarily limited, when compared against the correct or more preferred definition presented in the foregoing encyclopedia.

As example, the dictionary defines a gel as a colloid in a more solid form than a sol, and defines a sol as a fluid colloidal system. But the dictionary also defines a colloid as a substance that is in a state of division preventing passage through a semipermeable membrane, consists of particles too small for resolution with an ordinary light microscope, and in suspension or solution fails to settle out and diffracts a beam of light. The previously cited encyclopedia describes the colloid as a system of which one phase is made up of particles having dimensions of between 1 and 1,000 nanometers and is dispersed in a different phase. However, the size of the antibody coated magnetic beads in the preferred embodiment is four and one-half microns in size (e.g. 4,500 nanometers) and are capable of being viewed using an optical (light) microscope. Those coated magnetic beads would thus not qualify as a colloid under either Webster's definition or that of the encyclopedia. Carried to the extreme, the use of Webster's dictionary of thixotropic seem to preclude one from referring to the catsup as thixotropic. That would not be correct, and that dictionary should not be used to interpret the meaning of the terminology unless Webster's corrects the definition to include not only a gel but also a viscous fluid.

Catsup was selected as the preferred embodiment of the thixotropic non-Newtonian fluid since that substance is the only appropriate one that falls within our knowledge and experience. Other suitable thixotropic non-Newtonian fluids, whether preexisting or which may be developed in the future, that will be suitable as a replacement or substitute for catsup may be found or identified by others, who given the benefit of this description, would seek to improve upon the present invention or process. As example, other thixotropic non-Newtonian fluids that would be useful in the procedure include cross-linked acrylic polymers, organoclays, seaweed derivatives and xanthan gum.

It is believed that the foregoing description of the preferred embodiments of the invention is sufficient in detail to enable one skilled in the art to make and use the invention without undue experimentation. However, it is expressly understood that the detail of the elements comprising the embodiment presented for the foregoing purpose is not intended to limit the scope of the invention in any way, equivalents to those elements and other modifications thereof, all of which come within the scope of the invention, will become apparent to those skilled in the art upon reading this specification. Thus, the invention is to be broadly construed within the full scope of the appended claims.

What is claimed is:

1. A primary antibody bead suspension of an enzyme-linked immunoassay procedure comprising:
    a quantity of primary antibody coated magnetic beads;
    a volume of thixotropic fluid: and
    said coated magnetic beads being relatively uniformly dispersed within said volume of thixotropic fluid and being held in suspension by said thixotropic fluid and wherein said thixotropic fluid comprises the condiment known as catsup.

2. A primary antibody bead suspension of an enzyme-linked immunoassay procedure comprising:
    a quantity of primary antibody coated magnetic beads;
    a volume of thixotropic fluid: and
    said coated magnetic beads being relatively uniformly dispersed within said volume of thixotropic fluid and being held in suspension by said thixotropic fluid and being spherical in shape and of a diameter no greater than four and one-half microns in diameter; and wherein said thixotropic fluid comprises the condiment known as catsup.

* * * * *